United States Patent [19]

Maximenko et al.

[11] Patent Number: 4,564,596
[45] Date of Patent: Jan. 14, 1986

[54] UROKINASE DERIVATIVES COVALENTLY BOUND TO FIBRINOGEN

[76] Inventors: Alexandr V. Maximenko, Proezd Karamzina, 1, korpus 3, kv. 59; Elena G. Tischenko, ulitsa Eniseiskaya, 15, kv. 25; Vladimir P. Torchilin, Rostovskaya naberezhnaya, 1, kv. 90; Vladimir N. Smirnov, Juzhinsky pereulok, 3, kv. 7; Evgeny I. Chazov, 3 Cherepkovskaya, 15a, all of Moscow, U.S.S.R.

[21] Appl. No.: 705,343
[22] PCT Filed: Mar. 1, 1984
[86] PCT No.: PCT/US84/00008
    § 371 Date: Jan. 3, 1985
    § 102(e) Date: Jan. 3, 1985
[87] PCT Pub. No.: WO84/04536
    PCT Pub. Date: Nov. 22, 1984

[30] Foreign Application Priority Data

May 10, 1983 [SU] U.S.S.R. ............... 3590957

[51] Int. Cl.$^4$ .................. C12N 9/72; C12N 11/02; A61K 37/48
[52] U.S. Cl. .................. 435/177; 435/188; 435/215; 424/94
[58] Field of Search .............. 435/177, 188, 215; 424/94

[56] References Cited

U.S. PATENT DOCUMENTS

| | | | |
|---|---|---|---|
| 3,544,427 | 12/1970 | Sloane | 435/215 |
| 4,011,142 | 3/1977 | Jacobi | 435/215 X |
| 4,029,767 | 6/1977 | Vairel et al. | 435/215 X |
| 4,244,943 | 1/1981 | Yamahira et al. | 435/188 X |
| 4,286,063 | 8/1981 | Suyama | 435/188 X |
| 4,349,630 | 9/1982 | Maximenko et al. | 435/215 X |
| 4,381,346 | 4/1983 | Huasin et al. | 435/215 |

FOREIGN PATENT DOCUMENTS 113488 5/1979 Japan.
1022988 6/1983 U.S.S.R..

Primary Examiner—Howard E. Schain
Attorney, Agent, or Firm—Burgess, Ryan & Wayne

[57] ABSTRACT

Urokinase derivatives comprise urokinase covalently bonded with fibrinogen or urokinase covalently bonded with fibrinogen through an aliphatic diamine and correspond to the general formula:

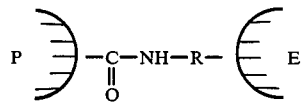

wherein P is fibrinogen, E is urokinase, R is absent or stands for

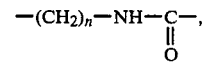

wherein n is 1-12, with a molecular mass of from 360,000 to 440,000 D, a content of protein of 10 to 30% by mass, an esterase catalytic activity of 30-60%.

These derivatives have an increased affinity to fibrin and feature a prolonged fibrinolytic effect.

7 Claims, No Drawings

UROKINASE DERIVATIVES COVALENTLY BOUND TO FIBRINOGEN

FIELD OF THE INVENTION

The present invention relates to bio-organic chemistry and, more particularly, to novel urokinase derivatives possessing affinity for thrombus material and displaying a thrombolytic activity.

BACKGROUND OF THE INVENTION

Known in the art are various urokinase derivatives, for example, water-soluble urokinase derivatives suitable for therapeutic purposes comprising complexes of the enzyme of urokinase with heparin or dextran sulphate (cf. U.S. Pat. No. 4,106,992; 1978; Japanese Pat. No. 159387, 1977).

These urokinase derivatives are, however, unstable.

When penetrating into blood circulation, they cause destruction of electrostatic interactions with the formation of substantially a mixture of urokinase with the vehicle, which is accompanied by a rapid inactivation of the enzyme and discontinuation of the thrombolytic effect.

Also known in the art are urokinase derivatives comprising urokinase covalently bonded with dextran (cf. Japanese Pat. No. 54-113488, 1979).

These derivatives are water-soluble and feature an enhanced stability. However, such modification of the enzyme does not ensure its affinity for the thrombus material, wherefore an enhanced fibrinolytic activity of blood with the use of such derivatives still does not guarantee an effective process of thrombolysis.

DISCLOSURE OF THE INVENTION

The present invention is directed to novel urokinase derivatives featuring an increased affinity for fibrin and possessing a prolonged fibrinolytic effect owing to a higher stability thereof.

The urokinase derivatives according to the present invention are novel and hitherto unknown in the literature.

The derivatives of urokinase according to the present invention comprise urokinase covalently bonded with fibrinogen, or urokinase covalently bonded, through an aliphatic diamine, with fibrinogen and corresponding to the general formula:

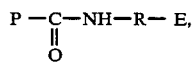

wherein P is fibrinogen, E is urokinase, R is either absent or stands for

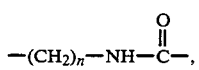

where n is 1 to 12; with a molecular mass of 360,000–440,000D, protein content of 10–30% by mass, and an esterase catalytic activity of 30 to 60%.

The compounds according to the present invention comprise a product of bonding of urokinase to fibrinogen which is employed as a vehicle for immobilization of urokinase.

Owing to proper selection of a matrix of a high-molecular vehicle (fibrinogen) the compounds according to the present invention have an increased tropism to the thrombus material. This ensures an effective progress of the thrombolytic process. At the same time, a preliminary modification of fibrinogen with aliphatic diamines hinders destruction of the protein matrix in the course of fibrinolysis. The addition of urokinase of fibronogen imparts an increased stability to the compounds which can also ensure prolongation of the fibrinolytic activity of such derivatives. As regards their kinetic parameters, the compounds according to the present invention are close to the native enzyme and in their fibrinolytic effect they are nearly two times more effective as compared to the starting urokinase.

DETAILED DESCRIPTION OF THE INVENTION

Properties of the novel compounds according to the present invention have been studied in in vitro experiments.

The experiment was carried out in parallel with the use of native urokinase and the following urokinase derivatives according to the present invention: compound 1 (urokinase attached to fibrinogen by means of 1,12-dodecamethylenediamine), compound 2 (urokinase added to fibrinogen by means of 1.10-decamethylenediamine), compound 3 (urokinase added to fibrinogen by means of 1,7-heptamethylenediamine), compound 4 (urokinase added to fibrinogen by means of 1,4-tetramethylene diamine), compound 5 (urokinase added to fibrinogen).

The study of kinetic parameters of an enzymatic hydrolysis of methyl ether of acetylglycyl lysine (AGLMe) by the compounds according to the present invention has shown that these compounds are very close to the native enzyme (urokinase). The data of the experiment are shown in Table 1 hereinbelow.

The AGLMe concentration is $10^{-3}$ to $10^{-2}$M, the enzyme concentration in the cell is 100 IU/ml.

As is seen from the data of Table 1, the best kinetic parameters of the urokinase derivatives according to the present invention are inherent in compound 1 (urokinase attached to fibrinogen by means of 1,12-dodecamethylenediamine). The use of the longest aliphatic diamine (the longest "leg") out of the available range of aliphatic diamines makes it possible to produce preparations having properties most resembling those of the native enzyme.

The long "leg" presumably eliminates to a considerable extent the negative effect provided on the enzyme globule by the matrix which might be revealed in a change of the conformation state of the combined enzyme molecule, in steric hindrances emerging upon the interaction of the enzyme with the substrate, and so forth.

TABLE 1

| Kinetic parameters | Native urokinase | Urokinase derivative of fibronogen and 1,12-dodecamethylenediamine (compound 1) | Urokinase derivative of fibrinogen and 1.10-decamethylenediamine (compound 2) | Urokinase derivative of fibrinogen and 1,7-heptamethylenediamine (compound 3) | Urokinase derivative of fibrinogen and 1,4-tetramethyldiamine (compound 4) | Urokinase derivative of fibrinogen (Compound 5) |
|---|---|---|---|---|---|---|
| 1 | 2 | 3 | 4 | 5 | 6 | 7 |
| $K_M$, M | $3.0 \times 10^{-4}$ | $11.0 \times 10^{-4}$ | $13.0 \times 10^{-4}$ | $14.0 \times 10^{-4}$ | $15.0 \times 10^{-4}$ | $18.0 \times 10^{-4}$ |
| $k_{cat}$, sec$^{-1}$ | 62 | 33 | 30 | 29 | 27 | 21 |

This is proven by the comparison of kinetic characteristics of native urokinase and products of modification thereof. Thus, with shortening "leg" length values of $K_M$ for urokinase derivatives are increased and values of $k_{cat}$ are decreased. For compound 5 (urokinase combined with fibrinogen without a diamine) a maximum value of $K_M$ and a minimum value of $k_{cat}$ are characteristic which demonstrates a noticeable reduction in the activity of this derivative in comparison with native urokinase.

The addition of urokinase to fibrinogen shifts the pH-optimum of the enzyme catalytical activity relative to hydrolysis of the AGLMe towards the acidic side. Thus, the pH-optimum of native urokinase is 8.3, the pH-optimum of the urokinase derivative according to the present invention (compound 1) is 7.5. This is explained by elimination of the negative charge of carboxy groups in a globule of urokinase upon activation thereof with carbodiimide. The alteration of the residual catalytical activity of urokinase upon its modification occurs in the following manner: enzyme activity prior to modification—100%, after the stage of carbodiimide activation—88%, after combining with fibrinogen modified with 1,12-dodecamethylenediamine—57%, after separation of the resulting derivative by the utrafiltration method on an "Amicon" instrument is 52%. The combining of the enzyme with the polymetric matrix of fibrinogen makes it possible to retain, for the enzyme globule, a certain mobility (changes of $K_M$, $k_{cat}$) and, in addition, it imparts an increased stability to the resulting biocatalyst compound which is demonstrated by the data of the following Table 2.

TABLE 2

| Compounds | Residual catalytic activity retained by the preparation upon incubation at 50° C. in a 0.1M phosphate buffer with pH = 7.5 after: | | | | |
|---|---|---|---|---|---|
| | 3 hours | 7 hours | 14 hours | 24 hours | 48 hours |
| Native urokinase | 80 | 56 | 38 | 10 | — |
| Compound 1 | 85 | 75 | 60 | 47 | 32 |
| Compound 2 | 86 | 75 | 56 | 49 | 37 |
| Compound 3 | 86 | 73 | 58 | 45 | 40 |
| Compound 4 | 88 | 76 | 60 | 52 | 42 |
| Compound 5 | 90 | 78 | 66 | 56 | 44 |

The determination of the residual catalytic activity was carried out in a pH-stat by hydrolysis of a $10^{-3}$M solution of AGLMe in a 0.1M KCl at the pH=7.5 and at room temperature.

The experimental determination of the thrombolytic activity of compounds of native urokinase and the derivatives of urokinase according to the present invention was effected according to the procedure described in the USSR Inventor's Certificate No. 824023 with the addition, to the washing solution, of 0.33 mg/ml of human plasminogen. To 0.5 ml of a solution (10 mg/ml) of fibrinogen 0.2 ml of a solution (4 mg/ml) of thrombin is added and this mixture is maintained for one hour at room temperature; during this time the fibrin skeleton of the thrombus is formed. It is placed onto a permeable film into a secured plastic tube with a diameter of 1.0–1.5 cm with its bottom washed by 15 ml of a solution of a 0.15M phosphate buffer with the pH of 7.4. In this solution plasminogen is also dissolved (0.33 mg/ml; control) and preparations of native urokinase and derivatives of urokinase according to the present invention which are used in a ratio ensuring their similar esterase (AGLMe) catalytic activity. The dissolution of the fibrin clot is controlled by an increase in the optical density (at $\lambda = 280$ nm) of the washin solution with time. The results of the experiments are shown in Table 3.

TABLE 3

| Time, min | Native urokinase | | | Compound of the present invention (urokinase - 1,12-dodecamethylenediamine-fibrinogen) | | |
|---|---|---|---|---|---|---|
| | $A^{280}$ | $\Delta A^{280}$ | % | $A^{280}$ | $\Delta A^{280}$ | % |
| 0 | 0.292 | 0 | 0 | 0.842 | 0 | 0 |
| 30 | 0.326 | 0.034 | 11 | 0.879 | 0.037 | 12 |
| 90 | 0.383 | 0.091 | 30 | 0.971 | 0.129 | 43 |
| 150 | | | | 1.083 | 0.241 | 80 |
| 180 | 0.418 | 0.126 | 42 | 1.144 | 0.302 | 100 |
| 240 | 0.484 | 0.192 | 64 | | | |
| 270 | 0.539 | 0.247 | 82 | | | |
| 300 | 0.592 | 0.300 | 100 | | | |

The ratio of the increment of the optical density of the solution (as a result of destruction of the insoluble fibrin clot and passing of its fragments into solution upon thrombolysis) to the time period during which it occurred characterizes the speed of the thrombolysis process in such a system (tgα). In a control experiment no considerable lysis of a fibrin clot is observed. For preparations of native urokinase and the derivatives of urokinase according to the present invention (compound 1) the values of tgα are equal to 0.3 and 0.5 respectively which points to a high thrombolytic activity of the derivative of urokinase according to the present invention and it is also proven by the values of duration of a complete dissolution of a thrombus equal to 5 and 3 hours respectively.

The final results of the experiments on thrombolysis are shown in Table 4 hereinbelow.

TABLE 4

| Preparation | Speed of dissolution of fibrin clot | Time of complete dissolution of fibrin clot, hours |
|---|---|---|
| Native urokinase | 0.3 | 5 |
| Compound 1 | 0.5 | 3 |
| Compound 2 | 0.43 | 4 hrs 45 min |
| Compound 3 | 0.40 | 4 |

TABLE 4-continued

| Preparation | Speed of dissolution of fibrin clot | Time of complete dissolution of fibrin clot, hours |
|---|---|---|
| Compound 4 | 0.36 | 4 hrs 20 min |
| Compound 5 | 0.25 | 5.5 |

The data shown in Table 5 demonstrate that with the growth of the "leg" length of the employed diamine the efficiency of the thrombolytic action of the urokinase derivatives according to present invention is increased. It might be suggested that the reason of this phenomenon resides in a more favourable ratio, for such derivatives, of the enzyme mobility, its distance from the vehicle matrix and its ability of being built in the thrombus material. It is likely that a further increase of the "leg" length is inadvisable, since the stabilizing effect of the vehicle is lost and modification thereof by such bifunctional reagents with increasing hydrophobicity is hindered due to shortening of their actual length (twisting of the methylene chain). As experimental data show, 12 methylene groups in the reagent chain is the length of an intermolecular cross-linking which is close to the optimal one.

The experimental verification of the enhanced tropism of the preparation has been effected in the following manner: formed clots of fibrin were washed for a specified period of time (15 minutes) with solutions of preparations of native urokinase and the derivatives of urokinase according to the present invention. Then the clots were transfered into solutions of the same buffer without the enzyme and incubated for three hours. In these solutions the growth of optical density was determined, i.e. the speed of dissolution of the fibrin clot; as the control use was made of a buffer containing plasminogen and washing the fibrin clot during the entire duration of the experiment. It has been shown that there occurs a rapid building-in of fibrinogen from the washing solution into the fibrin clot. This inclusion is detected visually already within 5–15 minutes. The results of the experiments are shown in Table 5 hereinbelow.

It follows from the data of Table 5 that the effect of the native preparation of urokinase ($tg\alpha = =0.15$) as regards the efficiency of thrombolysis, is close to the data of the control experiment ($tg\alpha = =0.14$). Fibrinolysis in the control is due to the presence of plasmin impurity in the plasminogen preparation. A considerably higher thrombolytic activity is revealed by the urokinase derivative—compound 1 ($tg\alpha = 0.3$). It means that this very derivative of urokinase has an affinity towards the fibrin clot, since it is included thereinto upon the first 15-minutes' incubation and transfered along with the clot into the buffer solution, wherein the fibrinolytic action of the preparation lasts for 3 hours.

TABLE 5

| Preparation | Speed of dissolution of fibrin clot within 3 hours in a buffer solution after incubation with the preparation during: | | | | |
|---|---|---|---|---|---|
| | 15 min | 15 min | 15 min | 15 min | 15 min |
| Native urokinase | 0.15 | 0.17 | 0.14 | 0.16 | 0.14 |
| Compound 1 | 0.3 | 0.38 | 0.42 | 0.44 | 0.46 |
| Compound 2 | 0.22 | 0.26 | 0.28 | 0.30 | 0.31 |
| Compound 3 | 0.19 | 0.22 | 0.24 | 0.25 | 0.27 |
| Compound 4 | 0.16 | 0.20 | 0.23 | 0.25 | 0.26 |
| Compound 5 | 0.11 | 0.12 | 0.12 | 0.14 | 0.15 |

TABLE 5-continued

| Preparation | Speed of dissolution of fibrin clot within 3 hours in a buffer solution after incubation with the preparation during: | | | | |
|---|---|---|---|---|---|
| | 15 min | 15 min | 15 min | 15 min | 15 min |
| Control | 0.14 | 0.14 | 0.14 | 0.14 | 0.14 |

Moreover, upon repetition of the experiment with the same fibrin clots for several times (up to 5) it has been observed that the urokinase derivatives according to the present invention have the ability of being additionally built into an already lyzed thrombus which is proven by increasing values of $tg\alpha$ (from 0.3 to 0.46)—characteristic indicator of the thrombolysis efficiency. As it is seen from Table 5, a similar ability is not inherent in native urokinase.

The process for producing the urokinase derivatives according to the present invention is performed in a conventional manner.

The process is carried out in three stages.

(I) Activation of carboxy groups of fibrinogen by means of a carbodiimide and addition of an aliphatic amine thereto.

This process is performed by a conventional technique.

To a solution of fibrinogen in distilled water (pH=3.8) a 100-fold molar excess of 1-ethyl-3-(3-dimethylaminopropyl)carbodiimide is added and the mixture is incubated for 10 minutes at room temperature, whereafter it is added with a 100-fold molar excess of an aliphatic amine in a phosphate buffer (pH=8.3) at the temperature of 4° C. and pH=4.5 and the incubation is continued for 5 hours. The resulting product (product 1) is dialyzed against distilled water at 4° C., then against the phosphate buffer at pH=8.3.

(2) Activation of carboxy groups of urokinase by means of a carbodiimide.

To a soution of urokinase preliminarily dialyzed against distilled water and a phosphate buffer (pH=8.3) 1-ethyl-3-(dimethylaminopropyl)carbodiimide is added in the molar ratio of 1:100 and incubation is effected at the temperature of 4° C. for 20 minutes (product II).

(3) Addition of urokinase immobilized with respect to fibrinogen.

The reaction of combining of urokinase and fibrinogen is effected by mixing products I and II, followed by incubation of the mixture for 18 hours at the temperature of 4° C. Then the resulting preparation of urokinase covalently bonded with fibrinogen is recovered by means of gel-chromatography or ultrafiltration on an instrument "Amicon" with the filter XM-100.

The above-described process for producing urokinase derivatives is illustrated by the following scheme.

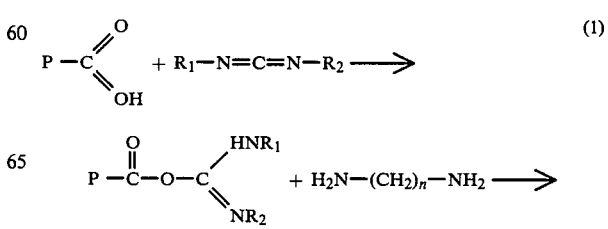

-continued

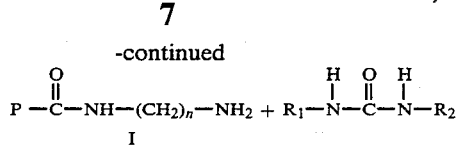

wherein P — is fibrinogen protein.

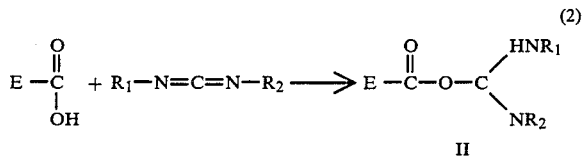

wherein E — is urokinase enzyme.

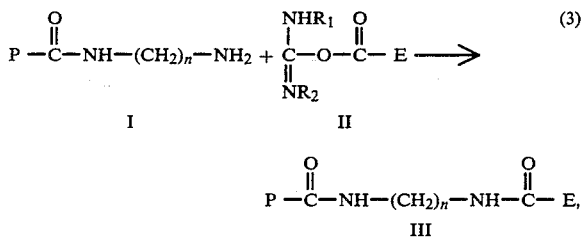

Gel-chromatographic recovery of the obtained derivatives in a column packed with Sephadex G-100 has shown an increase of the molecular mass of the product (360–440 thousand D) as compared to native urokinase (31,000–54,000D). This points to the covalent addition of urokinase to fibrinogen (the product was recorded both through the protein (280 nm, spectrophotometry) and through the esterase catalytical activity of urokinase).

At the same time, the comparison of properties of the resulting derivatives (Tables 1, 2 and 4) has shown that urokinase directly attached to fibrinogen (without a diamine "leg", compound 5) is distinguished, by a number of features, from derivatives of the enzyme attached to the vehicle matrix by means of a diamine.

Thus, the trends in variation of $K_M$ and $k_{cat}$, as shown hereinabove, point to an enhanced steric influence of the vehicle on catalytical properties of urokinase. A higher thermal stability of the product (compound 5) proves a more rigid attachment of urokinase to fibrinogen in this case. The fibrinolytic activity of compound 5 in this case is lower than in compounds 1–4 which manifests a limited mobility of the enzyme in this situation. The above-mentioned facts prove that the addition of urokinase to fibrinogen in compounds 1 to 4 is effected through the "leg" of the aliphatic diamine.

The obtained urokinase derivatives after lyophilization comprise a white floccular powder readily soluble in water.

The resulting derivatives of urokinase according to the present invention have a molecular weight of 360,000–440,000D, protein content—10–30% by mass, esterase catalytic activity—30–60%.

The synthesis of urokinase derivatives covalently bonded with fibrinogen through an aliphatic diamine makes it possible to produce derivatives of the enzyme possessing a high thrombolytic activity, an increased stability and affinity towards the thrombus material.

Such derivatives of urokinase comprise effective agents for a systemic thrombolysis of a prolonged effect.

For a better understanding of the present invention the following examples of urokinase derivatives and procedures of their preparation are given hereinbelow by way of illustration.

EXAMPLE 1

7.83 mg of fibrinogen are dissolved in 6 ml of distilled water ($3.8 \times 10^{-6}$M) at room temperature, the solution is acidified by means of HCl to the pH=3.8 and then 4 mg of a carbodiimide are added thereto. 10 minutes thereafter, when the solution pH reaches its maximum value (pH=4.5) 2 ml of the solution of activated fibrinogen are taken and added at the temperature of 4° C. to 2 ml of a solution of 1,12-dodecamethylenediamine ($3.8 \times 10^{-4}$M) in a 0.1M phosphate buffer (pH=8.3) and the mixture is incubated for 5 hours. Thereafter the incubation mixture is subjected to dialysis for 2 hours at a low temperature first against distilled water and then, under the same conditions, against a 0.02M phosphate buffer at the pH=8.3 (product I).

The preparation of urokinase (24,000 IU) is dissolved in 2 ml of distilled water and dialyzed at a low temperature for 2 hours against distilled water and then for additional 2 hours—against a 0.05M phosphate buffer with the pH=8.3. The dialyzed solution of urokinase is added with 4 mg of carbodiimide and the mixture is incubated at a low temperature under stirring for 20 minutes (product II).

Thereafter, the solution of activated urokinase (product II) is added with 2 ml of a solution of fibrinogen-1,12-dodecamethylenediamine (product I). The mixture is incubated for 18 hours at the temperature of 4° C., whereafter the resulting preparation is recovered from the reaction mixture by means of ultrafiltration on an "Amicon" instrument with the filter XM-100. A product is thus obtained which comprises urokinase covalently bonded with fibrinogen by means of 1,12-dodecamethylenediamine. The molecular mass is 440,000D, the content of protein is 10% by mass, the retained esterase catalytic activity is 50% as calculated for the starting urokinase.

EXAMPLE 2

The process is conducted in a manner similar to that described in Example 1, except that as the crosslinking agent 1,10-decamethylenediamine is used.

A product is thus obtained which comprises urokinase covalently bonded with fibrinogen by means of 1,10-decamethylenediamine. The molecular mass is 420,000D, the content of protein is 12% by mass, the retained esterase catalytic activity is 45% as calculated for the starting urokinase.

EXAMPLE 3

The process is conducted in a manner similar to that described in Example 1, except that as the cross-linking agent 1,7-heptamethylenediamine is used. A product is thus obtained which comprises urokinase covalently bonded with fibrinogen by means of 1.7-heptamethylenediamine. The molecular mass is 400,000D, the content of protein is 14% by mass, the retained catalytic esterase activity is 30% as calculated for the starting urokinase.

EXAMPLE 4

The procedure of Example 1 hereinbefore is repeated, except that as a cross-linking agent 1,4-tetramethylenediamine is used. A product is obtained which comprises urokinase covalently bonded with fibrinogen by means of 1,4-tetramethylenediamine. The molecular mass is 385,000D, the content of protein is 15% by mass, the retained esterase catalytic activity is 40% as calculated for the starting urokinase.

EXAMPLE 5

Urokinase is added to fibrinogen directly without any lengthening bridge of an aliphatic diamine.

2 ml of urokinase (12,000 IU/ml) are dialyzed for 2 hours at the temperature of 4° C. against distilled water and then against a 0.02M phosphate buffer with the pH of 8.3. The solution of urokinase is added with 2 ml of fibrinogen activated with carbodiimide ($3.8 \times 10^{-6}$M) and 1 ml of a 0.1M phosphate buffer with the pH=8.3. The mixture is incubated for 18 hours at the temperature of 4° C. The resulting derivative is recovered by ultrafiltration to give a product comprising urokinase covalently bonded with fibrinogen. The molecular mass is 360,000D, the content of protein is 30% by mass the retained esterase activity is 32% as calculated for the starting urokinase.

The urokinase derivatives according to the present invention featuring an increased affinity to fibrin and a protracted fibrinolytic effect can be used in medicine for the treatment of myocardial infarction, thromboses of coronary vessels, emboliae of lung arteries, thromboses of brain vessels and deep veins of limbs, and in a number of other cases.

We claim:

1. Urokinase derivatives comprising urokinase covalently bonded with fibrinogen or urokinase covalently bonded, through an aliphatic diamine, with fibrinogen of the general formula:

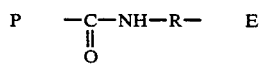

wherein P is fibrinogen, E is urokinase, R is either a single bond or stands for

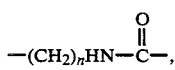

wherein n is 1–12, with a molecular mass of 360,000 to 440,000D, a content of protein of 10–30% by mass, and an esterase catalytic activity of 30–60%.

2. The urokinase derivative of claim 1 wherein said aliphatic diamine is 1,12-dodecamethylenediamine.

3. The urokinase derivative of claim 1 wherein said aliphatic diamine is 1,10-decamethylenediamine.

4. The urokinase derivative of claim 1 wherein said aliphatic diamine is 1,7-heptamethylenediamine.

5. The urokinase derivative of claim 1 wherein said aliphatic diamine is 1,4-tetramethylenediamine.

6. The urokinase derivative of claim 1 wherein R represents a single bond.

7. A process for the preparation of a urokinase derivative of the formula:

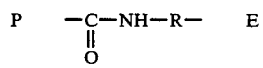

which comprises reacting a compound of the formula:

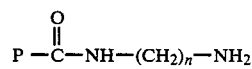

with a compound of the formula:

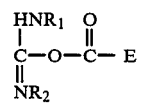

wherein P is fibrinogen, E is urokinase, R represents a single bond or

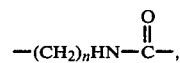

$R_1$ is $C_2H_5$, $R_2$ is

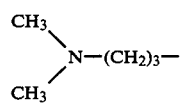

and n is 1–12, and recovering said derivative having a molecular mass of 360,000 to 440,000D, a protein content of 10–30% by mass, and an esterase catalytic activity of 30–60%.

* * * * *